United States Patent [19]

Breslin

[11] Patent Number: 4,775,318
[45] Date of Patent: Oct. 4, 1988

[54] TOOTH STORAGE MEANS

[76] Inventor: Daniel V. Breslin, 7934 Ridge Ave., Philadelphia, Pa. 19128

[21] Appl. No.: 239,220

[22] Filed: Mar. 13, 1986

[51] Int. Cl.[4] ............................................. A61C 19/10
[52] U.S. Cl. ..................................... 433/26; 206/63.5
[58] Field of Search ........................ 433/167, 26, 163; 206/63.5, 83, 477, 493, 368, 369

[56] References Cited

U.S. PATENT DOCUMENTS

| | | | |
|---|---|---|---|
| 1,702,312 | 2/1929 | Pickering | 206/83 |
| 1,771,271 | 7/1930 | Pommer | 248/158 |
| 2,184,977 | 12/1939 | Martin | 206/83 |
| 2,362,660 | 11/1944 | Moyer | 206/83 |
| 2,363,997 | 11/1944 | Rothman | 206/83 |
| 2,554,044 | 5/1951 | McNeill | 206/83 |
| 2,584,207 | 2/1952 | Hou | 63/27 |
| 2,620,919 | 12/1952 | Passmore | 206/83 |
| 2,705,815 | 4/1955 | Brauer | 433/6 |
| 2,874,487 | 2/1959 | Bloon | 434/263 |
| 3,009,265 | 11/1961 | Bezark | 434/270 |
| 3,111,760 | 11/1963 | Semmelman et al. | 433/26 |
| 3,460,252 | 8/1969 | Schneider et al. | 433/171 |
| 3,848,335 | 11/1974 | Bergersen | 433/196 |

OTHER PUBLICATIONS

T. P. Laboratories, Inc., Catalog 905, p. S-35, P.O. Box 73, LaPorte, Ind. 46350.

Primary Examiner—Robert Peshock
Attorney, Agent, or Firm—Jacob Trachtman

[57] ABSTRACT

A tooth storage means comprising a body having an upper section and a lower section, the upper section of the body having a downwardly extending portion providing a plurality of tooth elements corresponding to the upper teeth of a subject and the lower section of the body having an upwardly extending portion providing a plurality of tooth elements corresponding to the lower teeth of the subject. Each of the tooth elements has a receptacle cavity therein for receiving, storing and completely enclosing a corresponding individual tooth of the subject. The upper and lower tooth elements each have an appearance, arrangement and configuration corresponding to and simulating the upper and lower teeth of the subject and are of a transparent material allowing the display and viewing therethrough of the teeth of the subject received within respective cavities of the booth elements. The body has top and bottom covers which are removable and replaceable for completely enclosing the receptacle cavities of the upper and lower tooth elements respectively and for providing access thereto. The front vertical surface of the body is curved and has a mouth opening and lip portions simulating the upper and lower lips of a subject and the upper and lower tooth elements extend into the mouth opening from behind the lip portions for simulating the appearance of a subject.

23 Claims, 1 Drawing Sheet

TOOTH STORAGE MEANS

BACKGROUND OF THE INVENTION

The invention relates to a tooth storage means, and more particularly to a tooth storage means including a plurality of tooth elements having an appearance and arrangement corresponding to the teeth of a subject for receiving, storing and displaying same.

Heretofore, display holders and cases had been provided for storing artificial teeth. Display cards for artificial teeth have also been utilized for mounting and providing ready accessibility to a plurality of artificial teeth or sets of artificial teeth. Such devices, however, have not provided storage means for teeth comprising a plurality of tooth elements each having an appearance and arrangement corresponding to the teeth of a subject, and each of which tooth elements receives an individual corresponding tooth of a subject for storage and display, such as the primary or infant teeth of a child as they become available. Such prior art devices also fail to provide a storage means for teeth in which the tooth elements which have an appearance and arrangement corresponding to the teeth of a subject are provided with receptacle cavities for receiving and completely enclosing corresponding teeth of a subject and allowing the stored teeth to be displayed and viewed while stored. Such devices have also failed to provide for the addition of indicia to the storage means as it becomes available for disclosing information related to each of the individual teeth stored therein.

It is therefore a principal object of the invention to provide a new and improved tooth storage means for storing, retaining and displaying one or more teeth of a subject within a plurality of tooth elements which have an appearance, arrangement and configuration corresponding to the teeth of a subject.

Another object of the invention is to provide a new and improved tooth storage means providing a plurality of tooth elements each having a receptacle cavity for receiving, storing and retaining a respective individual tooth of a subject.

Another object of the invention is to provide a new and improved tooth storage means allowing the display and viewing of stored teeth in an arrangement and configuration corresponding to the natural teeth of a subject.

Another object of the invention is to provide a new and improved tooth storage means providing a plurality of tooth elements corresponding to the teeth of a subject and having a plurality of receptacle cavities for storing the teeth of a subject.

Another object of the invention is to provide a new and improved tooth storage means having a plurality of tooth elements having an appearance, arrangement and configuration corresponding to the teeth of a subject with respective receptacle cavities for storing and displaying the corresponding teeth of a subject while still stored therein.

Another object of the invention is to provide a new and improved tooth storage means in which a plurality of teeth of a subject may be stored and easily removed and replaced as desired.

Another object of the invention is to provide a new and improved tooth storage means having an appearance and configuration of a mouth with teeth therein which have receptacle cavities for receiving and displaying corresponding teeth of a subject.

Another object of the invention is to provide a new and improved tooth storage means allowing the displaying and viewing of the teeth stored therein simulating the appearance of the mouth region and teeth of a subject and having means for receiving indicia for providing information relating to the individual teeth stored therein.

Another object of the invention is to provide a new and improved tooth storage means which completely encloses and securely and safely retains therein the teeth of a subject.

Another object of the invention is to provide a new and improved tooth storage means which may readily be manufactured and is inexpensive to produce and is durable and rugged in structure.

SUMMARY OF THE INVENTION

The above objects and advantages, as well as many other advantages are achieved by providing a tooth storage means comprising a body having an upper section and a lower section. The upper section of the body has a downwardly extending portion providing a plurality of tooth elements protruding from an upper gum ridge corresponding to the upper teeth of a subject, and the lower section of the body has an upwardly extending portion providing a plurality of lower tooth elements protruding from a lower gum ridge and corresponding to the lower teeth of the subject. Each of the tooth elements has a receptacle cavity therein for receiving, storing and completely enclosing an individual corresponding tooth of the subject. The upper and lower tooth elements have an appearance, arrangement and configuration corresponding to the upper and lower teeth of a subject and are of a transparent material allowing the displaying and viewing therethrough of the teeth of a subject which are received and stored within respective cavities of the tooth elements.

The upper and lower sections of the body have respective top and bottom surfaces. The cavities of the upper tooth elements of the upper section extend upwardly to the top surface each providing an opening therein for receiving therethrough a respective upper tooth of a subject. Similarly, the cavities of the lower tooth elements of the lower section extend downwardly to the bottom surface each providing an opening therein for receiving therethrough a respective lower tooth of a subject. The body has a top cover which is movable for controllably enclosing the top surface and the openings of the cavities of the upper tooth elements, and a bottom cover which is movable for controllably enclosing the bottom surface and the openings of the cavities of the lower tooth elements.

The body has substantially vertical front and rear surfaces, and the top and bottom surfaces of the upper and lower sections are substantially horizontal surfaces. The front surface of the body has a mouth opening communicating with a mouth cavity between its upper and lower sections simulating the mouth opening of a subject with the upper tooth elements of the upper section extending downwardly in the mouth cavity into the mouth opening of the body, and the lower tooth elements of the lower section extending upwardly in the mouth cavity into the mouth opening and toward the upper tooth elements. The front surface of the body is curved to correspond to the mouth region, the curved gum ridges and arrangement of the teeth of a subject, and the mouth opening has upper and lower edges which are spaced apart so that the upper and lower tooth elements are visibly exposed therethrough. The upper and lower edge regions of the mouth opening respectively simulate the upper and lower lips of a subject, and the upper tooth elements extend into the mouth opening from behind the upper lip while the lower tooth elements extend into the mouth opening from behind the lower lip.

In use, when the corresponding top and bottom covers are removed, teeth of a subject may be placed into the receptacle cavities of corresponding upper and lower tooth elements and securely retained therein by replacing its cover. Indicia relating to each of the teeth stored in the tooth elements may be provided on the top and bottom covers of the body, and the teeth stored within the storage means may be visibly seen through the transparent tooth elements in a corresponding arrangement within the mouth opening of the device.

BRIEF DESCRIPTION OF THE DRAWING

The foregoing and other objects of the invention will become more apparent as the following detailed description of the invention is read in conjunction with the drawing, in which.

Like reference numerals designate like parts throughout the several views.

DETAILED DESCRIPTION

Figure 1:
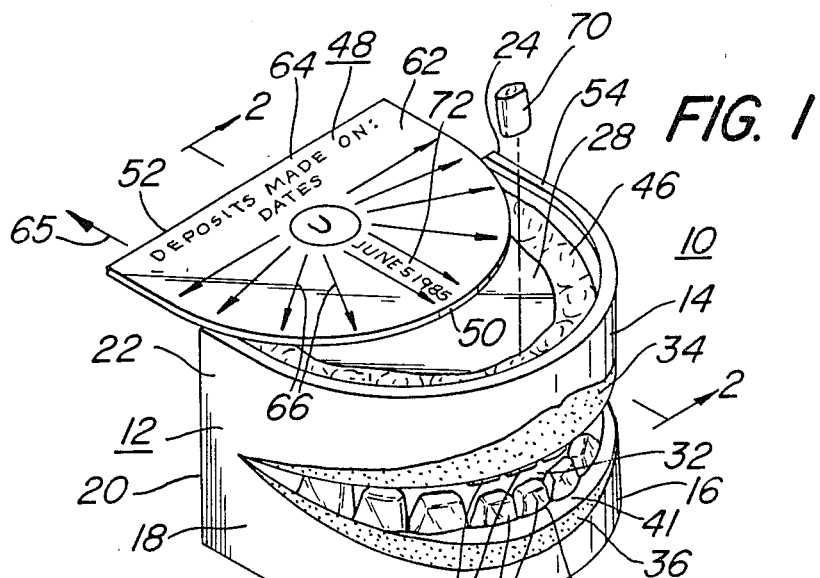
FIG. 1 is a perspective view of a tooth storage means embodying the invention with the top cover partially removed.

Referring to the figures, a tooth storage means 10 embodying the invention comprises a body 12 which may be made of a plastic or other suitable material. The body 12 has an upper section 14 and a lower section 16. The front surface 18 of the body 12 is substantially vertical and is curved to provide a portion of a substantially cylindrical surface with spaced apart ends 22 and 24. The body 12 has a rear substantially vertical plane surface 26 extending between the ends 22, 24 of the front surface 18. The upper section 14 of the body 12 has a top substantially horizontal surface 28, while the lower section 16 has a substantially horizontal bottom surface 30.

The curved front surface 18 of the body 12 has a mouth opening 32 extending horizontally between the ends 22 and 24. The opening 32 simulates the mouth opening of a human subject and narrows in the direction towards the ends 22 and 24 of the body 12. The mouth opening 32 communicates with a mouth cavity 33 between the upper and lower sections 14 and 16. The upper edge portion 34 of the mouth opening 32 is preferably formed to resemble the upper lip of a subject, while the lower edge portion 36 resembles the lower lip providing the appearance of the mouth in a partialy open position on the curved surface 18 corresponding to the mouth region of a subject. For increasing the attractiveness of the body 12, the front surface 18 may be made of a colored material or have applied thereto a surface layer colored to represent the face of the subject. The upper and lower edge portions 34 and 36 may also be colored to represent the lips of a subject.

The upper portion 14 of the body 12 is provided with a plurality of tooth elements 38 which protrude downwardly within the mouth cavity 33 from an upper gum ridge 39 located behind the upper edge portion 34 into the mouth opening 32, while the lower section has a plurality of lower tooth elements 40 which protrude upwardly within the mouth cavity 33 from a lower gum ridge 41 located behind the lower edge portion 36 of the lower section 16 and extend into the mouth opening 32 and toward the upper tooth elements 38.

The upper tooth elements 38 comprise a set which have an appearance, arrangement and configuration corresponding to the upper teeth of a huaan subject. Thus, each of the teeth elements 38 has an outer configuration resembling a particular one of the set of teeth of the subject and is adjacently arranged along the curved gum ridge 39 corresponding to that of the natural arrangement of teeth of a subject. This arrangement also provides for the tooth elements 38 to extend downwardly beyond the upper edge portion 34 of the mouth opening 32 to provide an appearance simulating a set of upper teeth within the mouth of a subject. Similarly, the lower teeth 40 comprise a set having the various configurations and arrangements corresponding to a set of lower teeth of a human subject, and are also positioned along the curved gum ridge 41 in opposing relationship to the upper tooth elements 38. The lower tooth elements 40, also extend upwardly beyond the lower edge portion 36 so that both the upper and lower sets of tooth elements 38 and 40 are clearly visible through the mouth opening 32 of the body 12. Thus, the set of upper and lower tooth elements 38 and 40 give the appearance of a set of upper and lower teeth as they naturally appear in a human subject.

Figures 2, 4:
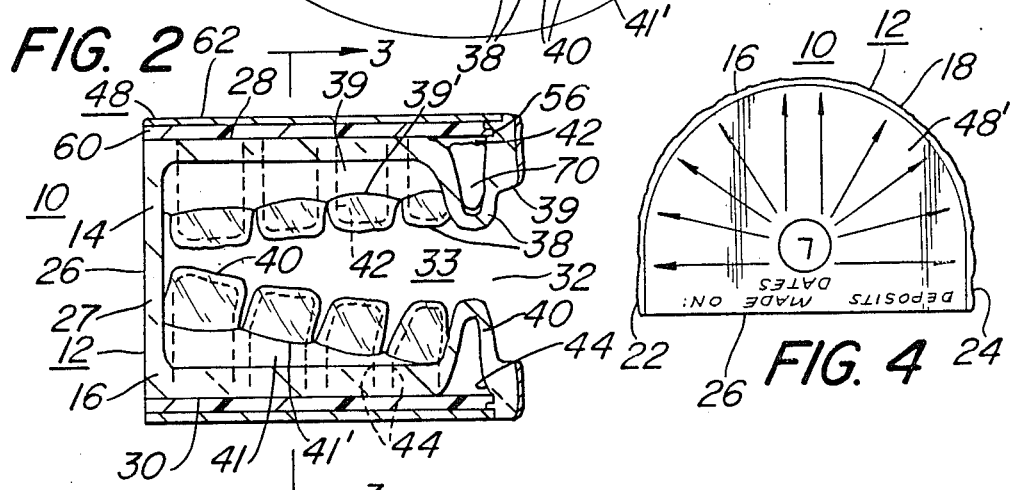
FIG. 2 is a sectional view taken on the line 2—2 of FIG. 1 with the top cover in its closed position.
FIG. 4 is a bottom plan view of the tooth storage means shown in FIG. 1.

Each of the upper tooth elements 38 has therein a receptacle cavity 42 which is sized and shaped to receive and enclose within it a corresponding tooth of the set of upper teeth of a subject, while the set of lower tooth elements 40 each also have corresponding receptacle cavities 44 of appropriate size and configuration for receiving therein the respective teeth of the subject. The receptacle cavities of the upper set of tooth elements 38 extend upwardly toward the top surface 28 forming respective openings 46 therein through which the corresponding teeth of the subject may be received into their receptacle cavities 42 of the tooth elements 38. The top surface 28 of the body 12 and the openings 46 are conditionally enclosed by a flat cover plate 48 having a curved front edge 50 and rear straight edge 52 corresponding with the curved and flat vertical front and rear surfaces 18 and 26 of the body. The upper section 14 of the body 12 is provided with an upwardly extending rim portion 54 having an inner groove 56 (FIG. 2). The cover plate 48 has an inner portion 60 with an extending edge 58 at the periphery for being slidably received in the groove 56 and is secured to an outer plate portion 62. When the cover plate 48 is slid outwardly in the direction of the arrow 65 (FIG. 1) and removed from the top of the upper section 14 of the body 12, the openings 46 are exposed, while the movement of the cover plate 48 in the direction opposite to that shown by the arrow 65 into the groove 56, encloses the top surface 28 and the opening 46 and retains and prevents the loss or dislodgment of the teeth stored within the receptacle cavities 42 of the tooth elements 38.

The cavities 44 of the lower set of tooth elements 40 which extend downwardly towards the bottom horizontal surface 30, provide corresponding openings 46' for allowing the delivery thereinto of corresponding teeth of the subject. A bottom cover plate 48' similar to the upper cover plate 48, is provided for conditionally covering the bottom surface 30 and enclosing the openings 46' therein. For this purpose, the bottom cover plate 48' has an inner plate portion 60' secured with an outer plate portion 62'. The inner plate portion 60' has an extending edge 58' slidably received within a corresponding groove 56' of a downwardly extending rim portion 54' of the lower section 16 of the body 12. The bottom cover plate 48' operates in a similar manner to allow access to the cavities 44 of the lower tooth elements 40, and when in place, encloses and secures therein against loss or removal the teeth contained within the receptacle cavities 44 (see FIG. 3).

The upper and lower cover plates 48, 48', may each be provided with indicia on its exposed outer surface 64 of its upper plate 62, 62' such as having the letters "U" and "L" for identifying the upper and lower covers 48, 48' and also corresponding to the upper and lower teeth of a subject. The surface 64 may also provide indicia including the words "DEPOSIT MADE ON: DATES" and a series of spaced angularly disposed arrows 66 each arranged to point to a particular one of the set of respective tooth elements 38, 40. The surface may also provide for a date to be written next to each of the arrows 66 for indicating when the tooth was deposited in the cavity of its corresponding tooth element 38, 40.

To provide the body 12 with a more realistic appearance, the upper gum ridge 39 is preferably colored to simulate the appearance of the upper gum of a subject and the tooth elements 38 which protrude downwardly therefrom define an upper gum line 39'. Similarly, the lower gum ridge 41 is similarly colored for simulating the lower gum of a subject and the tooth elements 40 protrude upwardly therefrom to define a lower gum line 41'. The gum lines 39' and 41' may be visible through the mouth opening 32 and within the mouth cavity 33. The tooth elements are preferably made of a clear transparent material allowing the viewing of teeth deposited within their receptacle cavities 42, 44. The tooth elements 38, 40, thus, by protruding from the colored gum ridges 39 and 41 also serve to provide a simulated appearance of a natural human mouth.

Figures 3, 5:
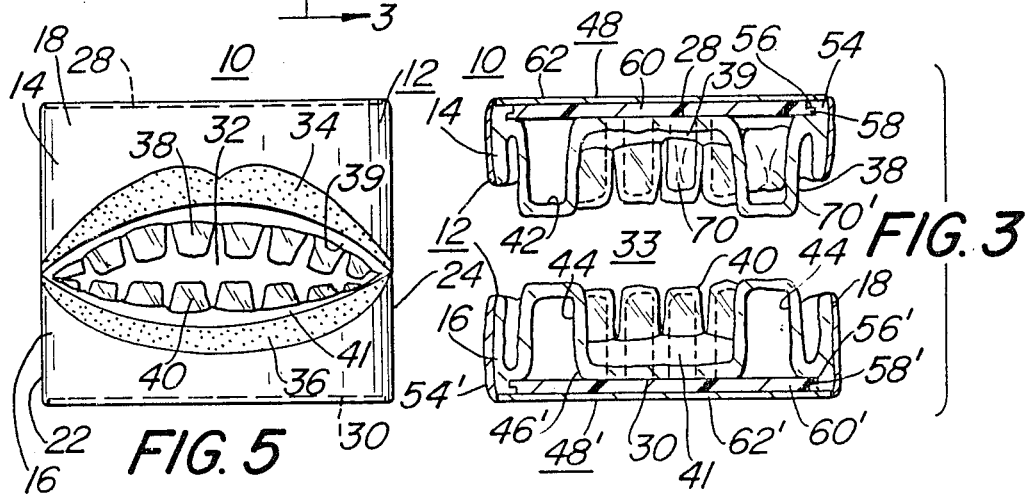
FIG. 3 is a sectional view taken on the line 3—3 of FIG. 2.
FIG. 5 is a front elevational view of the tooth storage means of FIG. 1.

Thus in operation, where for example, the tooth storage means 10 is utilized for storing the primary or infant teeth of a child, the storage means 10 is provided with the appropriate number of tooth elements corresponding to the infant teeth which are to be stored. This would correspond to ten (10) upper tooth elements 38 and ten (10) lower tooth elements 40, as shown by the figures. As each tooth is lost by the child, such as the tooth 70, it is deposited in its corresponding tooth element 38, a illustrated in FIG. 1. The date of deposit or loss of the tooth by the child, is recorded at a location 72 on the surface 64 of the cover plate 48, 48' proximate to an arrow 66 indicating a particular tooth element 38, 40. The tooth 70 is shown in FIGS. 2 and 3 within its cavity 42. Of course, as additional teeth are lost by the child, they are each deposited within a respective cavity as illustrated in FIG. 3 by the second tooth 70'. Eventually, the full set of primary teeth will be stored by the means 10 and preserved in the proper order, while being provided with indicia indicating the date in which each was deposited or lost by the child. Since the tooth elements 38, 40 are of a transparent material and each of the child's teeth is clearly visible within the mouth opening 32 of the body 12, there is no need to remove such teeth 70, 70' for viewing. This further reduces the probability of loss, damage or interchanging of the stored teeth.

The tooth storage means 10 also provides a highly utilitarian and desirable arrangement of the stored teeth corresponding to their natural positions in the subject's mouth before removal, while making them readily accessible should such need arise. A rear view of the stored teeth of a subject may also be obtained by providing the means 10 with a transparent relatively thin backwall 27. This allows the inspection of the teeth by looking into the mouth cavity 33 through the rear surface 26 of the body 10.

Although a particular form of the tooth storage means of the invention has been described in detail, it will be apparent that the disclosed means may be modified to provide for more or fewer tooth elements, and to accommodate the storage of adult teeth or teeth of animals should this be desired. The upper section 14 of the body 12 may also be separate and detached from the lower section 16 and utilized independently with or without the other, or they may be detachable one from the other, or provided with a hinged or articulating joint, where such modifications are desirable and depending upon various requirements and circumstances for utilizing the invention.

It will thus be seen that the objects set forth above and those apparent from a preceding description, are efficiently attained, and since certain changes may be made in the above apparatus without departing from the scope of the invention, it is intended that all matter contained in the above description shall be interpreted as illustrative and not in a limiting sense.

What is claimed is:

1. A tooth storage means comprising a body having an upper section and a lower section, the upper section of the body has a downwardly extending portion providing a plurality of individually distinct tooth elements having respective outer configurations corresponding to upper teeth of a subject and the lower section of the body has an upwardly extending portion providing a plurality of individually distinct tooth elements having respective outer configurations corresponding to lower teeth of the subject, each of the tooth elements has a receptacle cavity therein for loosely receiving and storing therein an individual corresponding tooth of the subject.

2. The tooth storage means of claim 1 in which the upper and lower tooth elements are respectively spaced and shaped to have an appearance, arrangement and configuration corresponding to a set of upper and lower teeth of a subject and are of a transparent material allowing the displaying and viewing therethrough of the teeth of a subject received within respective cavities of the tooth elements.

3. The tooth storage means of claim 2 in which the upper and lower sections of the body have respective top and bottom surfaces, the cavities of the upper tooth elements of the upper section of the body are each separate and distinct from each other and extend upwardly to the top surface for loosely receiving thereinto respective upper teeth of a subject and the cavities of the lower tooth elements of the lower section of the body are each separate and distinct from each other and extend downwardly to the bottom surface for loosely receiving thereinto respective lower teeth of a subject.

4. The tooth storage means of claim 22 in which the top and bottom covers respectively comprise top and bottom cover plates slidably engaging the body and respectively received over the top and bottom surfaces of the body, and each of the cover plates has an outer surface which provides for the receipt for indicia thereon relating to each of the teeth of a subject stored in respective tooth elements.

5. The tooth storage means of claim 1 in which the tooth elements have an appearance arrangement and configuration corresponding to upper and lower teeth of a subject and are of a transparent material allowing the displaying and viewing therethrough of the teeth of a subject received within respective cavities of the tooth elements.

6. The tooth storage means of claim 5 in which the front surface of the body has a curved surface corresponding to the curved arrangement of the teeth of a subject and the mouth opening has upper and lower edges which are spaced apart so that the upper and lower tooth elements are visually exposed therethrough.

7. The tooth storage means of claim 6 in which the upper and lower edges of the mouth opening have adjacent lip portions respectively simulating the upper lip and lower lip of a subject, and the upper tooth elements extend into the mouth opening from behind the upper lip portion and the lower tooth elements extend into the mouth opening from behind the lower lip portion.

8. The tooth storage means of claim 7 in which the upper and lower sections of the body have respective top and bottom surfaces, the cavities of the upper tooth elements of the upper section of the body extend upwardly to the top surface for receiving thereinto respective upper teeth of a subject and the cavities of the lower tooth elements of the lower section of the body extend downwardly to the bottom surface for receiving thereinto respective lower teeth of a subject.

9. The tooth storage means of claim 8 in which the body has a top cover which is movable for controllably enclosing the top surface and the cavities of the upper tooth elements, and a bottom cover which is movable for controllably enclosing the bottom surface and the cavities of the lower tooth elements.

10. The tooth storage means of claim 9 in which the top and bottom covers respectively comprise top and bottom cover plates slidably engaging the body and respectively received over the top and bottom surfaces of the body and each of the cover plates has an outer surface which provides for the receipt of indicia thereon relating to the teeth of a subject stored in respective tooth elements.

11. The tooth storage means of claim 5 in which the upper and lower sections of the body are connected by a rear wall portion providing the rear surface of the body, and the rear wall portion is of a transparent material permitting the viewing of the tooth elements therethrough.

12. The tooth storage means of claim 7 in which the upper section of the body has an upper gum ridge bordering the mouth opening behind the upper edge of the mouth opening providing the appearance of the upper gum ridge of a subject and the upper tooth elements protrudes downwardly therefrom into the mouth opening, and the lower section of the body has a lower gum ridge bordering the mouth opening behind the lower edge of the mouth opening providing the appearance of the lower gum ridge of a subject and with the lower tooth elements protruding upwardly therefrom into the mouth opening.

13. The tooth storage means of claim 12 in which the front surface, upper and lower lip portions, and the upper and lower gum ridges of the body have respective colors simulating those of a subject.

14. A tooth storage means comprising a body including a plurality of individually distinct tooth elements having respective configurations corresponding to a set of adjacently positioned teeth of a subject each of the tooth elements having a separate receptacle cavity therein for loosely receiving, completely enclosing therein, and storing an individual corresponding tooth of a subject.

15. A tooth storage means comprising a body including a plurality of individually distinct tooth elements spaced and shaped to have an appearance, arrangement and respective configurations corresponding to a set of adjacently positioned teeth of a subject each of the tooth elements having a separate receptacle cavity therein for loosely receiving and storing an individual corresponding tooth of a subject and are of a transparent material allowing the displaying and viewing therethrough of the teeth of a subject received within respective separate cavities of the tooth elements.

16. The tooth storage means of claim 15 in which the body has an outer surface and the cavities of the tooth elements are each separate and distinct from each other and extend to the outer surface for receiving thereinto respective teeth of a subject.

17. The tooth storage means of claim 16 in which the outer surface of the body has a cover securable with the body and movable for controllably enclosing the top surface of the body and cavities of the tooth elements while still allowing the display of the tooth elements.

18. The tooth storage means of claim 17 in which the cover comprises a cover plate which slidably engages the body and is received over the outer surface of the body, and the cover plate has an outer surface which provides for the receipt of indicia thereon relating to each of the teeth of a subject stored in respective tooth elements.

19. The tooth storage means of claim 18 in which the body has substantially vetical front and rear surfaces and the said outer surface of the body is a horizontal plane surface, the front surface of the body has a curved surface corresponding to the curved arrangement of the teeth of a subject.

20. The tooth storage means of claim 19 in which the tooth elements of the body are respectively spaced and shaped to have an appearance, arrangement and configuration corresponding to a set of adjacently positioned upper teeth of a subject.

21. A tooth storage means comprising a body including a plurality of tooth elements corresponding to a set of adjacently positioned teeth of a subject each of the tooth elements having a receptacle cavity therein for storing an individual corresponding tooth of a subject, the body has an outer surface and the cavities of the tooth elements extend to the outer surface for receiving thereinto respective teeth of a subject, the outer surface of the body has a cover which is movable for controllably enclosing the top surface of the body and cavities of the tooth elements, the cover comprises a cover plate which slidably engages the body and is received over the outer surface of the body, and the cover plate has an outer surface which provides for the receipt of indicia thereon relating to each of the teeth of a subject stored in respective tooth elements, the body has substantially vertical front and rear surfaces and the said outer surface of the body is a horizontal plane surface, the front surface of the body has a curved surface corresponding to the curved arrangement of the teeth of a subject, the tooth elements have an appearance, arrangement and configuration corresponding to a set of adjacently positioned lower teeth of a subject and are of a transparent material allowing the displaying and viewing therethrough of the teeth of a subject received within respective cavities of the tooth elements.

22. A tooth storage means comprising a body having an upper section and a lower section, the upper section of the body has a downwardly extending portion providing a plurality of tooth elements corresponding to upper teeth of a subject and the lower section of the body has an upwardly extending portion providing a plurality of tooth elements corresponding to lower teeth of the subject, each of the tooth elements has a receptacle cavity therein for receiving and storing an individual corresponding tooth of the subject, the upper and lower tooth elements have an appearance, arrangement and configuration corresponding to upper and lower teeth of a subject and are of a transparent material allowing the displaying and viewing therethrough of the teeth of a subject received within respective cavities of the tooth elements, the upper and lower sections of the body have respective top and bottom surfaces, the cavities of the upper tooth elements of the upper section of the body extend upwardly to the top surface for receiving thereinto respective upper teeth of a subject and the cavities of the lower tooth elements of the lower section of the body extend downwardly to the bottom surface for receiving thereinto respective lower teeth of a subject, the body has a top cover which is movable for controllably enclosing the top surface and the cavities of the upper tooth elements, and a bottom cover which is movable for controllably enclosing the bottom surface and the cavities of the lower tooth elements.

23. A tooth storage means comprising a body having an upper section and a lower section, the upper section of the body has a downwardly extending portion providing a plurality of tooth elements corresponding to upper teeth of a subject and the lower section of the body has an upwardly extending portion providing a plurality of tooth elements corresponding to lower teeth of the subject, each of the tooth elements has a receptacle cavity therein for receiving and storing an individual corresponding tooth of the subject, the body has substantially vertical front and rear surfaces, and its upper and lower sections have respective top and bottom horizontal plane surfaces, the front surface of the body has a mouth opening between its upper and lower sections simulating the mouth opening of a subject, the upper tooth elements of the upper section extend downwardly within the mouth opening of the body, and the lower teeth elements of the lower section extend upwardly within the mouth opening of the body and toward the upper tooth elements.

* * * * *

UNITED STATES PATENT AND TRADEMARK OFFICE
CERTIFICATE OF CORRECTION

PATENT NO. : 4,775,318
DATED : Oct. 4, 1988
INVENTOR(S) : Daniel V. Breslin

It is certified that error appears in the above-identified patent and that said Letters Patent is hereby corrected as shown below:

On the Title page item [21] should read -- Appl. No. 839,220 --

Signed and Sealed this

Twenty-seventh Day of April, 1993

*Attest:*

MICHAEL K. KIRK

*Attesting Officer*   Acting Commissioner of Patents and Trademarks